United States Patent
Albinali

(10) Patent No.: US 9,947,198 B2
(45) Date of Patent: Apr. 17, 2018

(54) SYSTEMS AND METHODS FOR CONTEXT-AWARE TRANSMISSION OF LONGITUDINAL SAFETY AND WELLNESS DATA WEARABLE SENSORS

(71) Applicant: EveryFit, Inc., Cambridge, MA (US)

(72) Inventor: Fahd Khalaf Albinali, Cambridge, MA (US)

(73) Assignee: Everyfit, Inc., Cambridge, MA (US)

( * ) Notice: Subject to any disclaimer, the term of this patent is extended or adjusted under 35 U.S.C. 154(b) by 661 days.

(21) Appl. No.: 14/010,281

(22) Filed: Aug. 26, 2013

(65) Prior Publication Data

US 2015/0054654 A1    Feb. 26, 2015

(51) Int. Cl.

| | | |
|---|---|---|
| G08B 1/08 | (2006.01) | |
| G08B 21/02 | (2006.01) | |
| H04W 4/00 | (2018.01) | |
| H04W 4/22 | (2009.01) | |
| A61B 5/00 | (2006.01) | |
| A61B 5/11 | (2006.01) | |
| G06F 19/00 | (2018.01) | |

(52) U.S. Cl.
CPC ............ G08B 21/02 (2013.01); A61B 5/0015 (2013.01); A61B 5/1118 (2013.01); A61B 5/681 (2013.01); H04W 4/008 (2013.01); H04W 4/22 (2013.01); A61B 5/1117 (2013.01); A61B 5/7282 (2013.01); A61B 2560/0209 (2013.01); A61B 2560/0276 (2013.01); G06F 19/3418 (2013.01); Y02B 60/50 (2013.01)

(58) Field of Classification Search
CPC ............................ G08B 21/02; G08B 21/0453
USPC .......... 340/573.1, 870.02; 455/67.11, 456.2; 600/483
See application file for complete search history.

(56) References Cited

U.S. PATENT DOCUMENTS

| | | | |
|---|---|---|---|
| 4,956,851 A | 9/1990 | Wolensky et al. | |
| 5,901,191 A | 5/1999 | Ohno | |
| 6,462,673 B1 | 10/2002 | Brooksby et al. | |
| 6,581,100 B1 | 6/2003 | Durin et al. | |

(Continued)

FOREIGN PATENT DOCUMENTS

| | | |
|---|---|---|
| EP | 1 700 281 | 9/2006 |
| EP | 1 870 864 | 12/2007 |

(Continued)

OTHER PUBLICATIONS

Albinali, Fahd, et al. "Using wearable activity type detection to improve physical activity energy expenditure estimation." Proceedings of the 12th ACM international conference on Ubiquitous computing. ACM, 2010.

(Continued)

*Primary Examiner* — Thomas McCormack
(74) *Attorney, Agent, or Firm* — Foley & Lardner LLP

(57) ABSTRACT

The present solution provides a system and a method for efficiently transmitting data recorded by a wearable sensor. More particularly, the systems and methods described herein enable the data/context-aware transmission of data. In some implementations, by classifying data into predefined categories and then transmitting the data using a transmitter configuration associated with each of the categories enables improved transmission reliability while also improving battery life.

22 Claims, 12 Drawing Sheets

(56) References Cited

U.S. PATENT DOCUMENTS

| | | | |
|---|---|---|---|
| 6,747,561 B1* | 6/2004 | Reeves | G06F 1/1626 340/573.1 |
| 6,771,694 B1 | 8/2004 | Baumgartner | |
| 7,103,806 B1 | 9/2006 | Horvitz | |
| 7,944,351 B1* | 5/2011 | Giallorenzi | G08B 25/014 340/539.11 |
| 8,044,013 B2 | 10/2011 | Schlingloff et al. | |
| 8,378,811 B2 | 2/2013 | Crump et al. | |
| 2007/0254593 A1* | 11/2007 | Jollota | A61B 5/14532 455/67.11 |
| 2010/0185101 A1* | 7/2010 | Sakai | A61B 5/02455 600/483 |
| 2013/0030711 A1 | 1/2013 | Korhonen | |
| 2013/0085348 A1 | 4/2013 | Devenyi et al. | |
| 2013/0285836 A1* | 10/2013 | Proud | H01F 38/14 340/870.02 |
| 2014/0106782 A1* | 4/2014 | Chitre | H04W 4/22 455/456.2 |

FOREIGN PATENT DOCUMENTS

| | | |
|---|---|---|
| EP | 1 894 175 | 3/2008 |
| EP | 2 310 959 | 4/2011 |
| WO | WO-01/84848 | 11/2001 |
| WO | WO-2013/089278 | 6/2013 |

OTHER PUBLICATIONS

Alireza Vahdatpour, et al., "Accelerometer-based on-body sensor localization for health and medical monitoring applications", Pervasive Mob Comput. Dec. 2011; 7(6): 746-760.

Bodhi Priyantha, et al., "Little Rock: Enabling Energy Efficient Continuous Sensing on Mobile Phones", Pervasive Computing IEEE 10.2 (2011) pp. 12-15.

Choi L., et al., "Validation of accelerometer wear and nonwear time classification algorithm", Med Sci Sports Exerc. Feb. 2011; 43(2): 357-64.

Daito Akimura, et al., "Compressed Sensing Method for Human Activity Sensing using Mobile Phone Accelerometers" 2012, IEEE.

Edward S. Sazonov, et al., "A Sensor System for Automatic Detection of Food Intake Through Non-Invasive Monitoring of Chewing", IEEE Sens J. 2012; 12(5): 1340-1348.

Guan-Zheng Liu, et al., "Estimation of Respiration Rate from Three-Dimensional Acceleration Data Based on Body Sensor Network", Telemedicine Journal and E-Health, Nov. 2011; 17(9): 705-711.

Jeremy W., "Wear Time Validation Parameters", Jul. 11, 2012, pp. 1-2, https://help.theactigraph.com/entries/21703957.

Jonathan Lester, et al., "Are You With Me?—using accelerometers to determine if two devices are carried by the same person" (2004), The College of Information Services and Technology, pp. 1-2.

Kai Kunze, et al., "Using acceleration signatures for everyday activities for on-body device location", 2007, Embedded Systems Lab, University of Passau, pp. 1-2.

Kristina Kowalski, et al., "Direct and indirect measurement of physical activity in older adults: a systematic review of the literature", International Journal of Behavioral Nutrition and Physical Activity 2012, 9:148.

Leena Choi, et al., "Validation of Accelerometer Wear and Nonwear Time Classification Algorithm", Med Sci Sports Exerc. Feb. 2011; 43(2) 357-364.

Mamaghanian, Hossein, et al. "Compressed sensing for real-time energy-efficient ECG compression on wireless body sensor nodes." Biomedical Engineering, IEEE Transactions on 58.9 (2011): 2456-2466.

Maurice R. Puyau, et al., "Validation and Calibration of Physical Activity Monitors in Children", (2002) Obesity Research, 10: 150-157.

Priyantha, N., Dimitrios Lymberopoulos, and Jie Liu. "Eers: Energy efficient responsive sleeping on mobile phones." Proceedings of PhoneSense 2010 (2010): 1-5.

Shelley S. Tworoger, et al., "Factors associated with objective (actigraphic) and subjective sleep quality in young adult women", Journal of Psychosomatic Research, vol. 59, Issue 1, Jul. 2005.

Stone KL, et al., "Actigraphy-measured sleep characteristics and risk of falls in older women", Arch Intern Med. Sep. 8, 2008; 168(16): 1768-1775.

Wang, Yi, Bhaskar Krishnamachari, and Murali Annavaram. "Semi-Markov state estimation and policy optimization for energy efficient mobile sensing." Sensor, Mesh and Ad Hoc Communications and Networks (SECON), 2012 9th Annual IEEE Communications Society Conference on. IEEE, 2012.

Wang, Yi, et al. "A framework of energy efficient mobile sensing for automatic user state recognition." Proceedings of the 7th international conference on Mobile systems, applications, and services. ACM, 2009.

Wang, Yi, et al. "Markov-optimal sensing policy for user state estimation in mobile devices." Proceedings of the 9th ACM/IEEE International Conference on Information Processing in Sensor Networks. ACM, 2010.

Yan, Zhixian, et al. "Energy-efficient continuous activity recognition on mobile phones: an activity-adaptive approach." Wearable Computers (ISWC), 2012 16th International Symposium on. IEEE, 2012.

Yang, Sungwon, and Mario Gerla. "Energy-efficient accelerometer data transfer for human body movement studies." Sensor Networks, Ubiquitous, and Trustworthy Computing (SUTC), 2010 IEEE International Conference on. IEEE, 2010.

* cited by examiner

SYSTEMS AND METHODS FOR CONTEXT-AWARE TRANSMISSION OF LONGITUDINAL SAFETY AND WELLNESS DATA WEARABLE SENSORS

A portion of the disclosure of this patent document contains material which is subject to copyright protection. The copyright owner has no objection to the facsimile reproduction by anyone of the patent document or the patent disclosure, as it appears in the file or records of the Patent and Trademark Office, but otherwise reserves all copyright rights whatsoever.

BACKGROUND OF THE DISCLOSURE

Medical alert devices are often marketed to the elderly as a means to stay in contact with caretakers and emergency services. The data provided by these devices can be highly beneficial in managing elderly (and patient) care. However, most medical devices operate in highly regulated frequency bands, which can present a number of challenges in efficiently transmitting high-resolution data.

BRIEF SUMMARY OF THE DISCLOSURE

The present solution provides a system and a method for efficiently transmitting data recorded by a wearable sensor. More particularly, the systems and methods described herein enable the data/context-aware transmission of data. In some implementations, by classifying data into predefined categories and then transmitting the data using a transmitter configuration associated with each of the categories enables improved transmission reliability while also improving battery life.

According to one aspect of the disclosure, a method for efficiently transmitting data from a wearable device includes classifying, by a wearable device with a transmitter configurable to transmit according to different transmission configurations, a first subset of data obtained by the wearable device. The subset of data is classified into a first category of a plurality of categories. Each of the plurality of categories corresponds to one of a plurality of transmission configurations. Each of the transmission configurations specify at least a power at which the transmitter is to transmit. The method also includes establishing, by the wearable device, the transmitter to use a first transmission configuration, and transmitting the first subset of data using the first transmission configuration. The method further includes establishing, by the wearable device responsive to classifying a second subset of data into a second category of the plurality of categories, the transmitter to use a second transmission configuration. The second transmission configuration is different from the first transmission configuration. The method also includes transmitting, by the transmitter, the second subset of data using the second transmission configuration.

In certain implementations, the method also includes transmitting to a receiver an indication of one of the first category or the first transmission configuration prior to transmitting the first subset of data. The method can also include transmitting to a receiver an indication of one of the second category or the second transmission configuration prior to transmitting the second subset of data.

In some implementations, the method includes encoding the first subset of data with a first encoding scheme specified by the first transmission configuration. In certain implementations, the method includes pausing for a predetermined amount of time after transmitting to the receiver the indication of one of the first category or the first transmission configuration.

In yet other implementations, the method includes obtaining, by the wearable device, the data from measurements via a motion sensor within the wearable device. The first subset of data can include a plurality of data points. The first subset of data can be classified based on the differences between consecutive data points within the plurality of data points.

In some implementations, each of the plurality of transmission configurations specifies at least one of a baud rate, a transmission frequency, a duty cycle of transmission or a receiving filter bandwidth. Classifying the first subset of data into the first category can be responsive to a context associated with the first subset of data. In certain implementations, the context is one of an age of a person wearing the wearable device, a time of day during which the first subset of data was captured, or an activity performed by the person wearing the sensor when the first subset of data was obtained.

In certain implementations, establishing the transmitter to use the first transmission configuration includes selecting a transmitter pre-configured to the first transmission configuration from a plurality of different transmitters on the wearable device.

According to another aspect of the disclosure, a wearable sensor device for efficiently transmitting data includes a transmitter configured to transmit according to different transmission configurations and a processor. The processor is configured to classify a first subset of data obtained by the wearable device into a first category of a plurality of categories. Each of the plurality of categories corresponds to one of a plurality of transmission configurations. Each transmission configuration specifies at least a power at which the transmitter is to transmit. The processor is also configured to establish the transmitter to use a first transmission configuration and transmit via the transmitter the first subset of data using the first transmission configuration. The processor then establishes the transmitter to use a second transmission configuration of the plurality of transmission configurations corresponding to the second category, the second transmission configuration different from the first transmission configuration. Then the transmitter transmits the second subset of data using the second transmission configuration.

In certain implementations, the processor is further configured to transmit, via the transmitter, to a receiver an indication of one of the first category or the first transmission configuration prior to transmitting the first subset of data. In other implementations, the processor is further configured to transmit, via the transmitter, to a receiver an indication of one of the second category or the second transmission configuration prior to transmitting the second subset of data.

In some implementations, the processor is further configured to encode the first subset of data with a first encoding scheme specified by the first transmission configuration, and to pause a predetermined amount of time after transmitting to the receiver the indication of the first category.

In yet other implementations, the processor is further configured to obtain the data via measurements from a motion sensor within the wearable device. The processor can classify the first and second subsets of data based on the differences between consecutive data points within respective subsets of data.

In some implementations, each of the plurality of transmission configurations specify at least one of a baud rate, a transmission frequency, a duty cycle of transmission or a receiving filter bandwidth. The processor can be configured to classify the first subset of data into the first category responsive to a context in which the first subset of data was recorded. The context can be one of an age of a person wearing the sensor, a time of day during which the first subset of data was captured, or an activity performed by the person wearing the sensor when the first subset of data was captured. In other implementations, processor is configured to select a radio configured to use the first transmission configuration.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following descriptions of the sections of the specification and their respective contents may be helpful:

For purposes of reading the description of the various embodiments below, the following descriptions of the sections of the specification and their respective contents may be helpful:

Section A describes a wearable sensor.

Section B describes a network environment and computing environment which may be useful for practicing embodiments described herein.

Section C describes an embodiment of a housing for a wearable sensor.

Section D describes embodiments of systems and methods for context-aware transmission of data from a wearable sensor.

A. Wearable Sensor Device

Prior to discussing specific embodiments of the present solution, it may be helpful to describe aspects of the device, operating environment, and associated system components (e.g., hardware elements) in connection with the methods and systems described herein.

Wearable sensor devices may be used to track physical activity, medical conditions, or be used as medical alert devices. The wear compliance of the sensor may be increased if the wearable sensor's battery life is extended. In some implementations, battery life can be extended through the power-efficient transmission of data. In some implementations, the power-efficient transmission of data includes transmission of data in a context or data aware fashion. For example, the data may be transmitted responsive to the type of data, content of the data, battery requirements, priority, or any combination thereof.

Figure 1A:
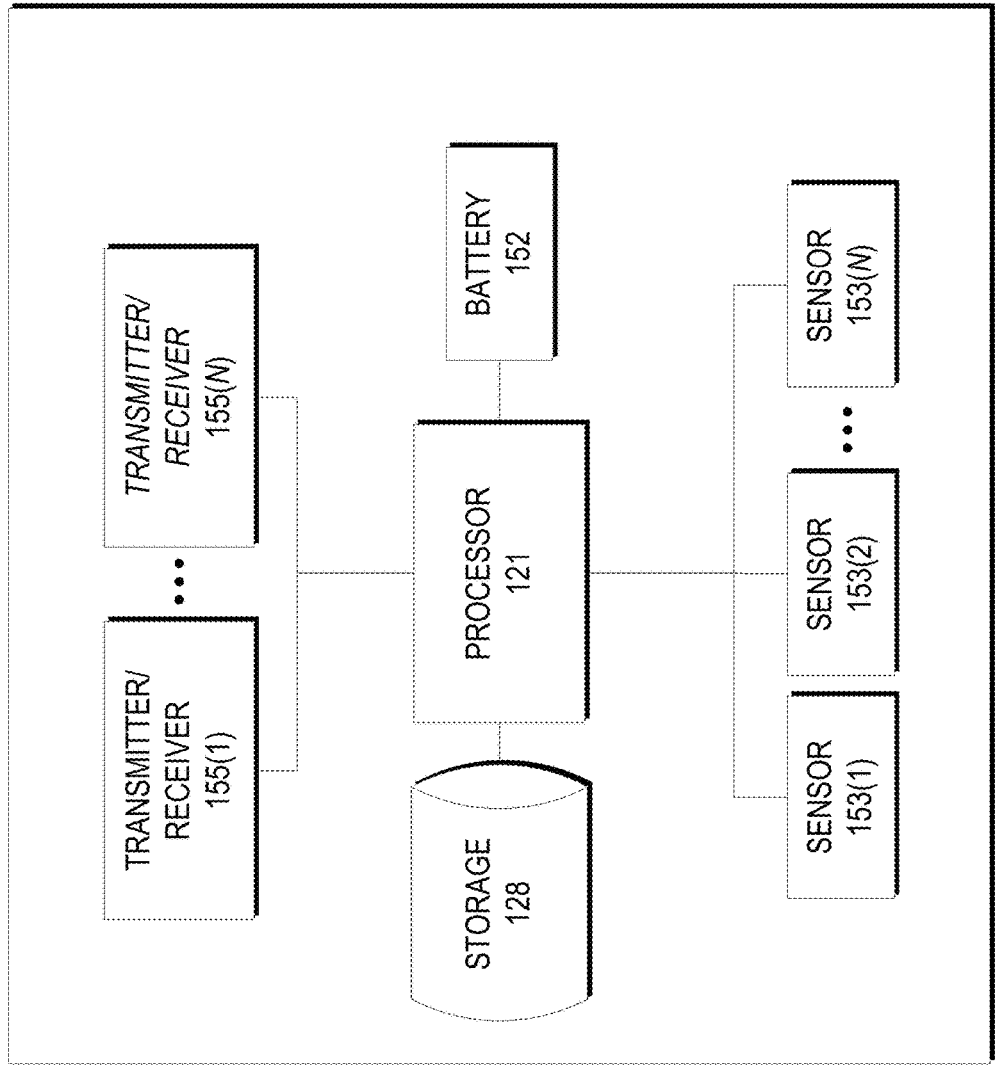
FIG. 1A is a block diagram of an embodiment of a wearable sensor.

FIG. 1A illustrates a block diagram of an embodiment of a wearable sensor 150. As described below, the outward form (i.e., housing) of the wearable sensor 150 can include many shapes, and in general may be reversibly coupled to a wearer. Internally, the wearable sensor 150 includes a processor (also referred to as a CPU) 121, which is powered by a battery 152. Also, the wearable sensor 150 can include a plurality of sensors 153(1)-153(N) (collectively referred to as sensors 153). The wearable sensor 150 can monitor behavioral and/or environmental conditions and store data into the storage device 128. The wearable sensor 150 can communicate with other devices through a data transmitter and receiver 155 module (also referred to as a TX/RX module 155).

Figure 1B:
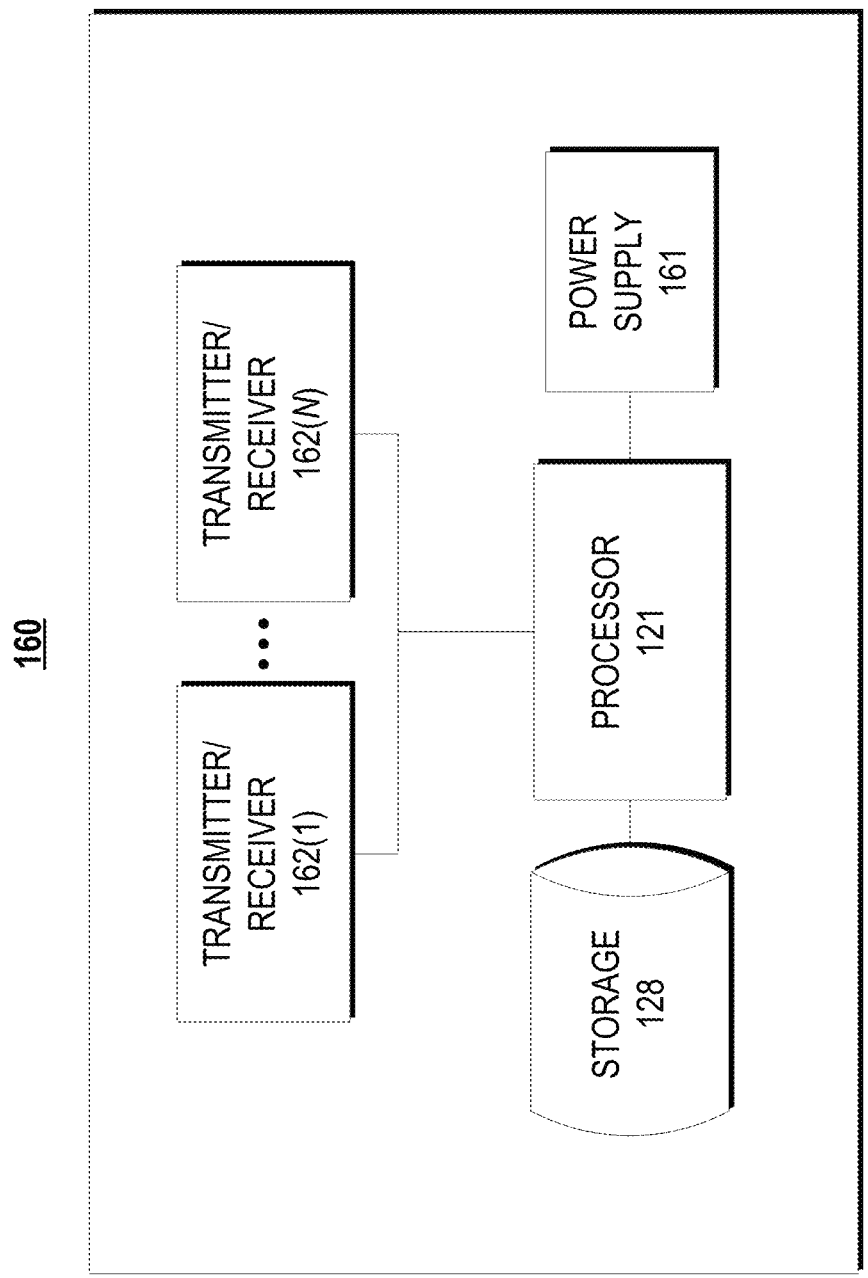
FIG. 1B is a block diagram of an embodiment of a base station.
Figure 1C:
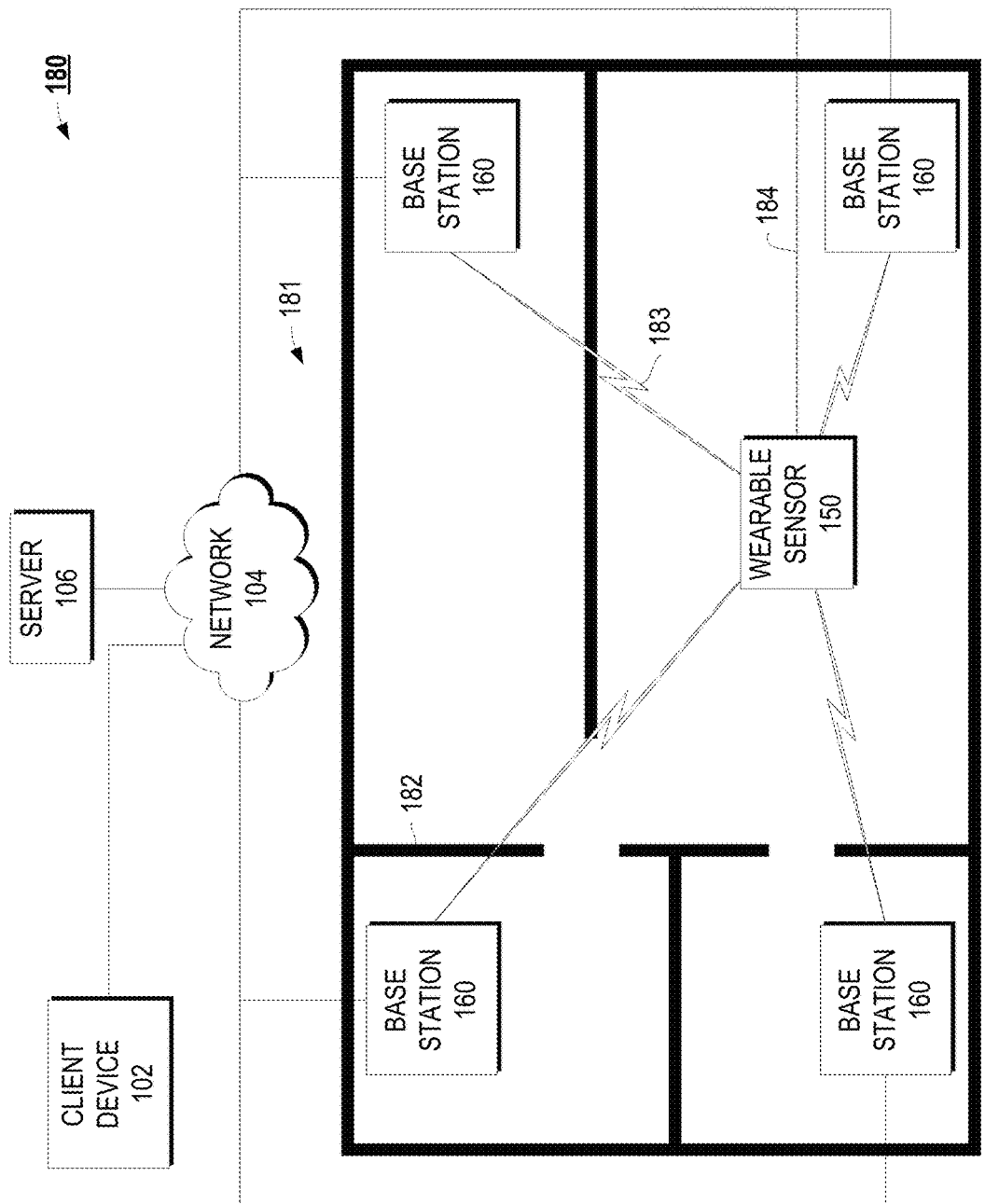
FIG. 1C is a schematic of an environment including the wearable sensor of FIG. 1A and base station of FIG. 1B.
Figure 1D:
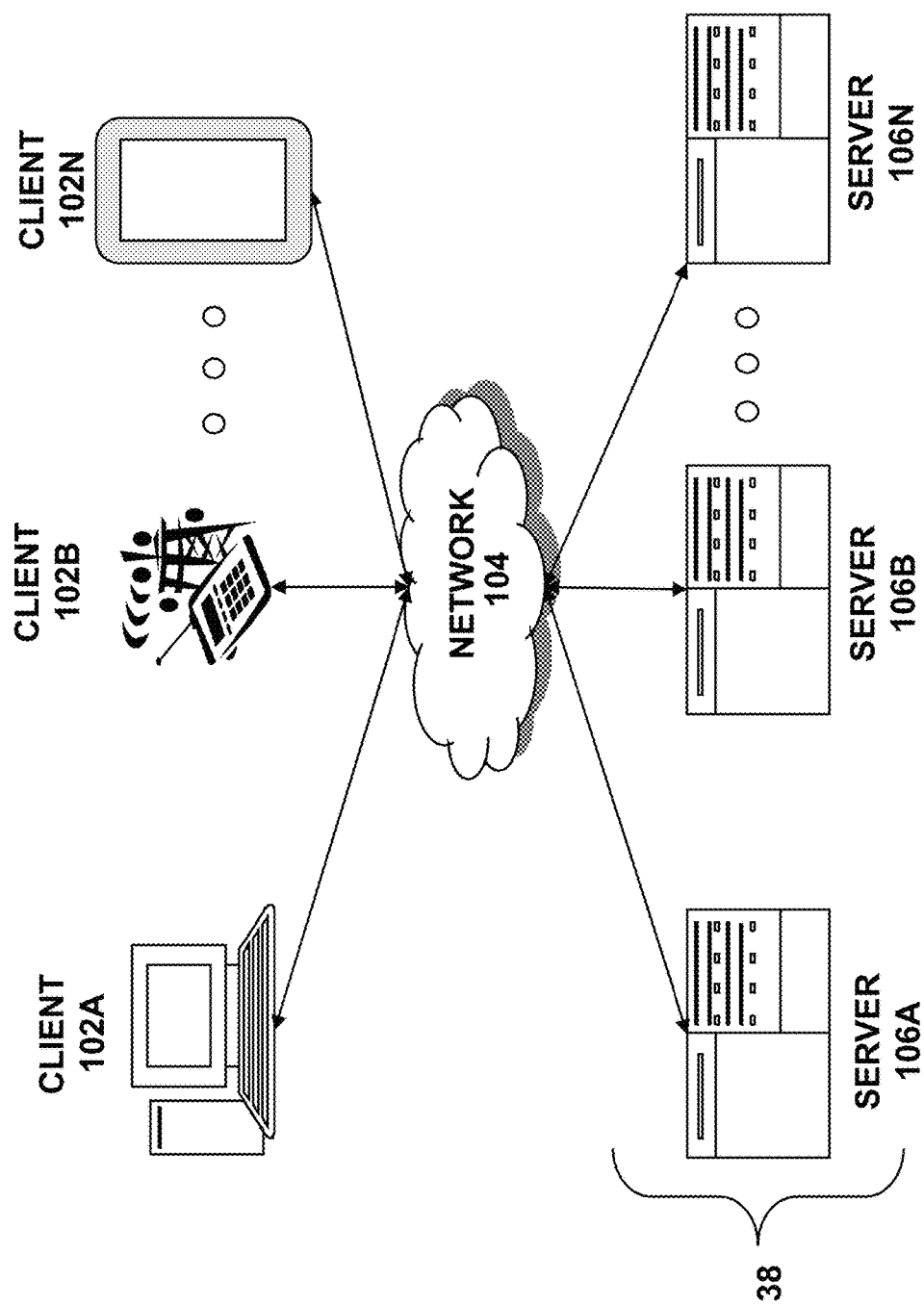
FIG. 1D is a block diagram depicting an embodiment of a network environment comprising client device in communication with server device.
Figure 1E:
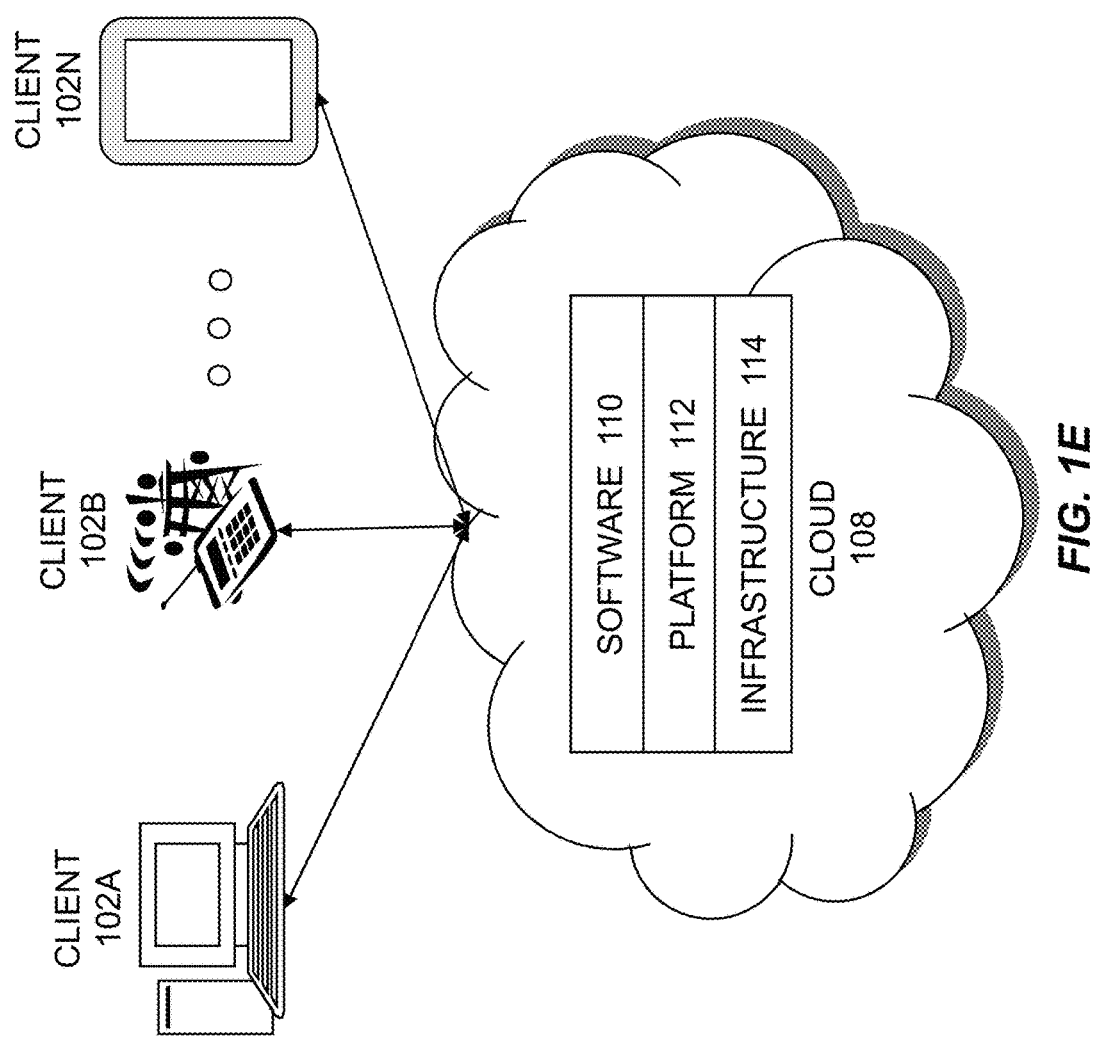
FIG. 1E is a block diagram depicting a cloud computing environment comprising client device in communication with cloud service providers.
Figure 1F:
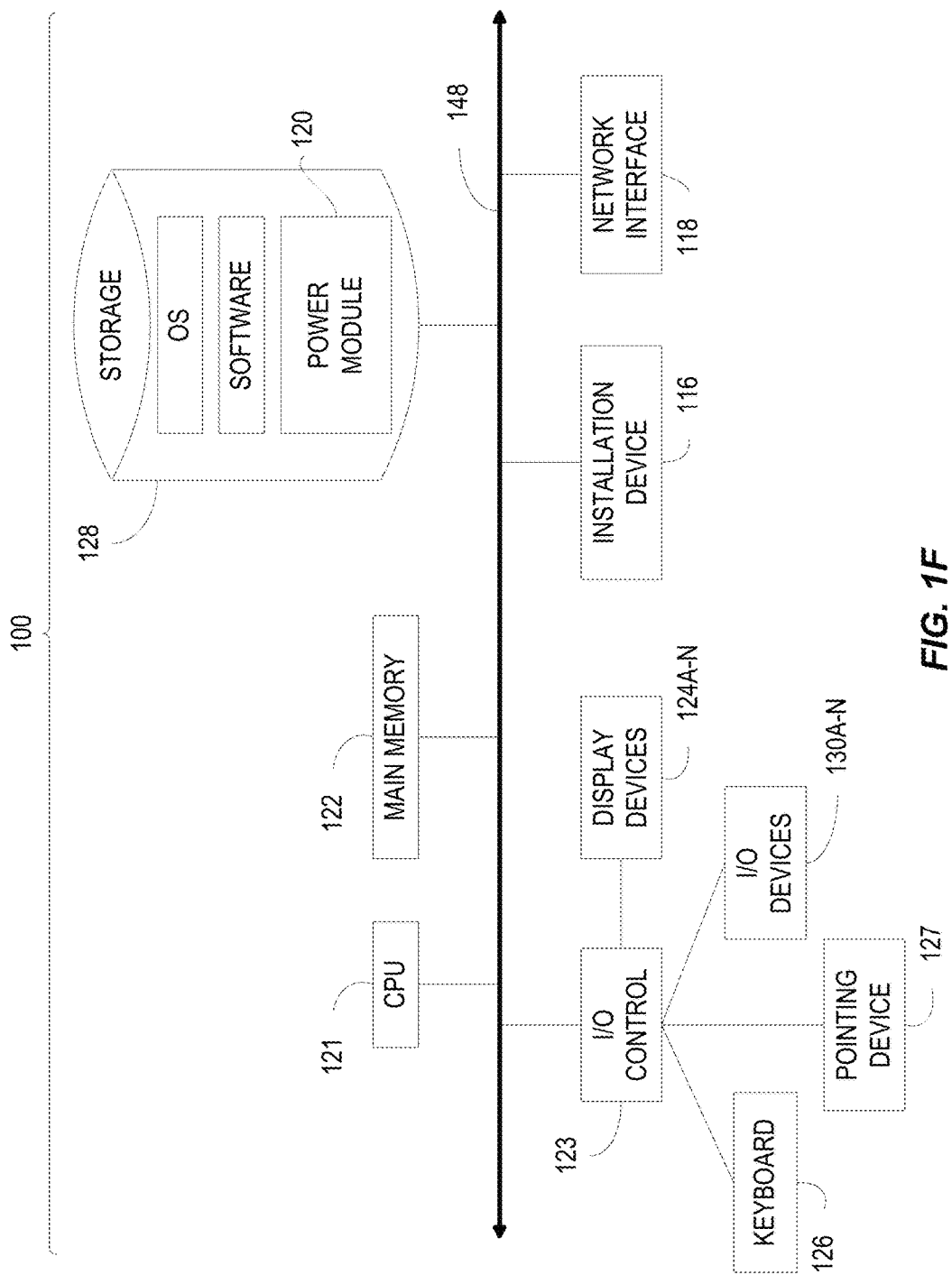
FIGS. 1F and 1G are block diagrams depicting embodiments of computing devices useful in connection with the methods and systems described herein.

The processor 121 and storage device 128 are discussed further in relation to FIGS. 1E and 1F, but in general the processor 121 is a microcontroller or central processing unit capable of executing the instructions and methods described herein. The processor 121 can include one or more analog to digital converters (A/D converters). The A/D converters may be used by the processor 121 to sample and record data from the plurality of sensors 153. In some implementations, the sensor 153 generates a digital signal, which the processor 121 can input without analog to digital conversion. Similarly, the storage device 128 may be any storage device capable of storing the instructions executed by the processor 121. In some implementations, the storage device 128 is a component of the processor 128.

In some embodiments, the storage device 128 is configured to store data obtained via the sensors 153 and/or calculations made by the processor 121. In some implementations, the storage device 128 is a stand-alone component. For example, the storage device 128 can be removeably coupled to the wearable sensor or it may be permanently coupled to the wearable sensor. For example, the storage device 128 may include a Secure Digital (SD) or other removable non-volatile memory card. In some implementations, the storage device 128 is a component of the processor 121. For example, the storage device 128 can be flash memory within the processor 121.

The wearable sensor 150 may store data in the storage device 128 prior to transmitting the data to a second device. For example, the wearable sensor 150 may transmit data to the second device at predetermined intervals (e.g., once every hour or day). In another example, the wearable sensor 150 may store data until the second device is in range, such that the data may be transferred to the second device. For example, the second device may be a base station located within the user's home. When the user (and wearable sensor 150) is away from their home, the wearable sensor 150 may store the data collected during that time onto the storage device 128. When the user arrives home the wearable sensor 150 may detect the base station and transmit the data to the base station. In some implementations, the storage device 128 is a circular storage device (e.g., a circular buffer), such that old data is automatically overwritten once the storage device 128 is full. For example, the storage device 128 may maintain the most recent day, week, or month's worth of data. In some implementations, the data stored in the buffer is divided into a plurality of subsections (e.g., newest, recent, and old data). The wearable sensor 150 may transmit one or more of the subsections to the base station responsive to a policy. For example, the wearable sensor 150 may automatically retransmit older data stored in the circular buffer when sending new data to ensure that the old data was properly received at the base station.

The wearable sensor 150 also includes TX/RX module 155. As described below, the TX/RX module 155 enables the wearable sensor 150 to communicate with other devices.

The other devices can include other wearable sensors 150, base stations, mobile phones, computers, servers, or any combination thereof. In some implementations, the wearable sensor 150 includes a plurality of TX/RX modules 155. For example, the wearable sensor 150 may include a WiFi radio and a Bluetooth radio for wireless communication and also include a universal serial bus (USB) for wired connections to other devices. In some implementations, the TX/RX modules 155 may use IEEE 802.11, Zigbee, USB, Bluetooth, Bluetooth low energy (e.g., v4), TCP/IP, sub-1 GHz (e.g. 315 MHz 433 Mhz 900 MHz) protocols such as SimpliciTI, or any combination thereof to communicate with other devices. One of ordinary skill in the art will recognize that other wired and/or wireless communication protocols may be used in the methods and systems described herein. In some implementations, the TX/RX module 155 is a component of the processor 121.

Power is supplied to the wearable sensor 150 by a battery 152 (or similar power storage device). In some implementations, the battery 152 is coupled to an energy harvester that collects environmental energy (e.g., a solar cell on the face of the wearable sensor 150). The battery 152 can supply between about 1.5 V and 9 V to the processor 121 and/or other components of the wearable sensor 150. In some implementations, the battery 152 lasts about 1-3, 2-5, 4-10, or 7-14 days before needing replacement or recharging. In other implementations, the battery 152 can last 2-6 months, 3-9 months, 8-12 months, or 1-3 years without replacement or recharging. In some implementations, the battery 152 may be a rechargeable battery. In some implementations, the rechargeable battery is charged through the above described USB port that may also be used for wired communication. The battery may be a disposable battery (e.g., a coincell battery). In some implementations, the wearable sensor 150 includes a plurality of batteries 152. The plurality of batteries 152 may be used to extend the time between battery replacement/recharging. In other implementations, one of the plurality of batteries 152 may act as a backup. For example, the backup battery may power the device in the event that the main battery 152 loses power. Similarly, the backup battery may power the wearable sensor 150 during periods of time when the main battery 152 is being replaced.

As illustrated in FIG. 1A, the wearable sensor 150 includes at least one sensor 153. The sensors 153 may be used to monitor and record a plurality of environmental parameters, physical activity parameters, behavioral parameters and medical parameters. For example, the sensors 153 enable the processor 151 to monitor factors such as temperature, light conditions, humidity, skin capacitance, skin resistance, UV light, air quality, ultrasound, FM/AM signal strength, heart rate, pulse oximetry, blood pressure, magnetometer, gas composition, pressure, altitude, breathing rate, force, location, proximity, or any combination thereof. In some implementations, the sensor 153 is a camera. The sensors 153 may measure physical activity parameters such as orientation, acceleration, position (relative or exact), number of steps taken over a period of time, overall activity level, impact (or shock) levels or any combination thereof.

The sensors 153 can include one or more of an accelerometer, gyroscope, passive vibration sensor, light sensor, temperature sensor, altitude sensor, and galvanic response sensor, GPS receiver, auditory sensors (i.e., microphone). The sensors 153 may be internal and/or external to the wearable sensor 150. For example, an accelerometer may be housed within the wearable sensor 150, while a light sensor may be disposed at least partially on the surface of the wearable sensor 150 such that it may detect the ambient lighting conditions. The processor 121 may sample the signal created by the sensors 153 at a plurality of sampling frequencies. For example, the processor 121 may sample the sensors 153 at about 0.25 Hz-5 Hz, 5 Hz-25 Hz, 25 Hz-50 Hz, 50 Hz-100 Hz, or greater than 100 Hz. In embodiments with a plurality of sensors 153, each of the sensors 153 may be sampled at a different frequency.

FIG. 1B illustrates an exemplary schematic of a base station 160 that may be used with the wearable sensor 150. The base station 160 may be a custom built device, general computing device and/or mobile phone. For example, the base station 160 may be any one of the below described client devices 102. As illustrated, the base station 160 may include one or more processors 121 and storage devices 128. The base station 160 also includes a power supply 161 and transmitters and receivers modules 162(1)-162(N) (collectively referred to as TX/RX modules 162). The power supply 161 can power the base station 160 through battery power and/or alternating current power. In some implementations, the base station 160 may include sensors similar to the above described sensors 153 of the wearable sensor 150.

The TX/RX modules 162 may be the similar to the TX/RX modules 155 in the wearable sensor 150. The TX/RX modules 162 may be configured to include a built-in network adapter, network interface card, PCMCIA network card, EXPRESSCARD network card, card bus network adapter, wireless network adapter, USB network adapter, modem or any other device suitable to communicating with devices and/or networks described herein. In some implementations, the base station 160 may include a first TX/RX module 162 that communicates with one or more wearable sensors 150 and a second TX/RX module 162 that communicates with a network.

FIG. 1C illustrates an environment 180 in which the wearable sensor 150 and base station 160 may be used. The environment 180 includes a structure 181 (e.g., a house), which includes a plurality of walls 182. As illustrated, each room of the structure 181 includes a base station 160. One of ordinary skill in the art will recognize that more than, or less than, four base stations 160 may be used with a base station 160. For example, a base station 160 may be configured to transmit a wireless signal that is detectable throughout substantially an entire house or structure. In other implementations, a wearable sensor 150 may be used without a base station 160.

The base stations 160 are in communication with a network 104. The connection may be wired or wireless. In some implementations, the communication between any two devices (e.g. a wearable sensor 150 and base station 160) in the environment 180 is encrypted. The environment 180 also includes at least one client device 102 and a server 106 are also connected to the network 104. The network 104 is described in greater detail below, but in general, the network 104 can include WANs, LANs, wired telephone networks, wireless telephone networks, or any combination thereof.

As illustrated, the wearable sensor 150 is in wireless communication with each of the base stations 160. In some implementations, the wearable sensor 150 may detect the signal 183 from each of the base stations 160, but only transmit data to a subset of the base stations 160 at any given time. In some implementations, the wearable sensor 150 and/or base stations 160 can determine the relative strength of the wireless connection between the wearable sensor 150 and base station 160. Using the relative strengths of the wireless connections, the relative position of the wearable sensor 150 can be determined. In some implementations, the relative strengths of the wireless connection is determined responsive to a received signal strength indication (RSSI) or a link quality indication (LQI). In some implementations, the relative position of the wearable sensor 150 can be determined using 1, 2, 3, 4, 5, or more base stations 160. For example, a user may have a first base station 160 located in their bedroom and a second base station 160 located in their living room. When the user and wearable sensor 150 are in the user's bedroom, the first base station 160 may have a relatively stronger connection to the wearable sensor 150 when compared to the second base station 160. Responsive to the relative connection strengths between the wearable sensor 150 and first base station 160 and wearable sensor 150 and the second base station 160 it can be determined that the user and wearable sensor 200 are located in the user's bedroom. In some implementations, a distribution of the RSSI and LQI within the environment 180 can be modeled. Applying, the wearable sensor's current wireless connection strength, the location of the wearable sensor 150 can be predicted using, for example, a particle filter.

The plurality of devices within the environment 180 are connected through the network 104. In some implementations, the wearable sensor 150 is connected to the network 104 through one or more base stations 160 via a wireless connection 183. In other implementations, the wearable sensor 150 is connected directly to the network 104 through connection 184. In yet other implementations, the wearable sensor 150 docks (or establishes a wired connection) with a base station 160 to connect to the network 104. For example, the base station 160 may collect data throughout the day. After data has been collected the user may transmit the collected data to the server 106 by connecting the wearable sensor 150 to a base station 160.

The wearable sensor 150 may communicate with other devices in the environment 180 to transmit data collected via the sensors 153. The wearable sensor 150 may establish a connection with one or more of the devices in the environment 180 at predetermined intervals (e.g., hourly, daily, weekly, or monthly), when the amount of data stored on its storage device 128 reaches a predetermined threshold, and/or the wearable sensor 150 may be in constant communication with the one or more devices when they are in range to enable wireless communication.

The environment 180 also includes a client device 102. Each of the client device 102, network 104, and server 106 are described in greater detail in relation to FIGS. 1E-1G. In brief, the client device 102 may include smart phones or other mobile devices. In some implementations, the client device 102 can also act as a base station 160. For example, the wearable sensor 150 may connect to the client device 102 via a Bluetooth connection to deliver data to the client device 102. The client device 102 may then establish a connection with the server 106 to deliver the data to the server 106. In some implementations, the client device 102 is in the possession of the user of the wearable sensor 150 and, in other implementations, the client device 102 is in the possession of a person other than the user of the wearable sensor 150. The environment 180 may include a plurality of client devices 102 that each correspond to a single wearable sensor 150. For example, a first client device 102 may be owned by the user of the wearable sensor 150 and a second client device 102 may be owned by a care taker of the user. Notifications or data corresponding to the wearable sensor 150 may be viewed by both the user and the care taker via their respective client devices 102.

In some implementations, the client device 102 may be used as an interface to the wearable sensor 150. The client device 102 may execute an application that enables a user to interact with the wearable sensor 150. The interaction may include turning the wearable sensor 150 on or off, marking events, viewing data, enabling features, or any combination thereof. In some implementations, a user can use the application to share and view data from (or with) loved-ones. Caretakers or medical professionals may use the application to view data from a patient. The application may also be used to transmit medical alters responsive to their detection by the wearable sensor 150. For example, the wearable sensor 150 may obtain motion data via a sensor 153 and transmit the data to the server 106. The user may view the trend of the motion data via the user's client device 102. In some implementations, alerts, updates, or data from an associated wearable sensor 150 is pushed to the client device 102. For example, the wearable sensor 150 may be configured to detect if the wearable sensor 150 is not being worn. If the wearable sensor 150 determines that it is not being worn, an alert may be sent to the client device 102 of a caretaker.

One of ordinary skill in the art will recognize that the methods described herein may occur on the wearable sensor 150, base station 160, client device 102, server 106, or any combination thereof. For example, the wearable sensor 150 may record motion data and transmit the data to the server 106. The server 106 may process the data to determine the wear state of the wearable sensor 150.

B. Computing and Network Environment

Prior to discussing specific embodiments of the present solution, it may be helpful to describe aspects of the operating environment as well as associated system components (e.g., hardware elements) in connection with the methods and systems described herein. Referring to FIG. 1E, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1E shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, public switching telephone network, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store. In some embodiments, one or more servers 106 may process a distributed data set. The distributed data set may be distributed over one or more servers 106 or storage systems. In these embodiments, the servers 106 may use MapReduce or Hadoop to process the data.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Referring to FIG. 1F, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1G:
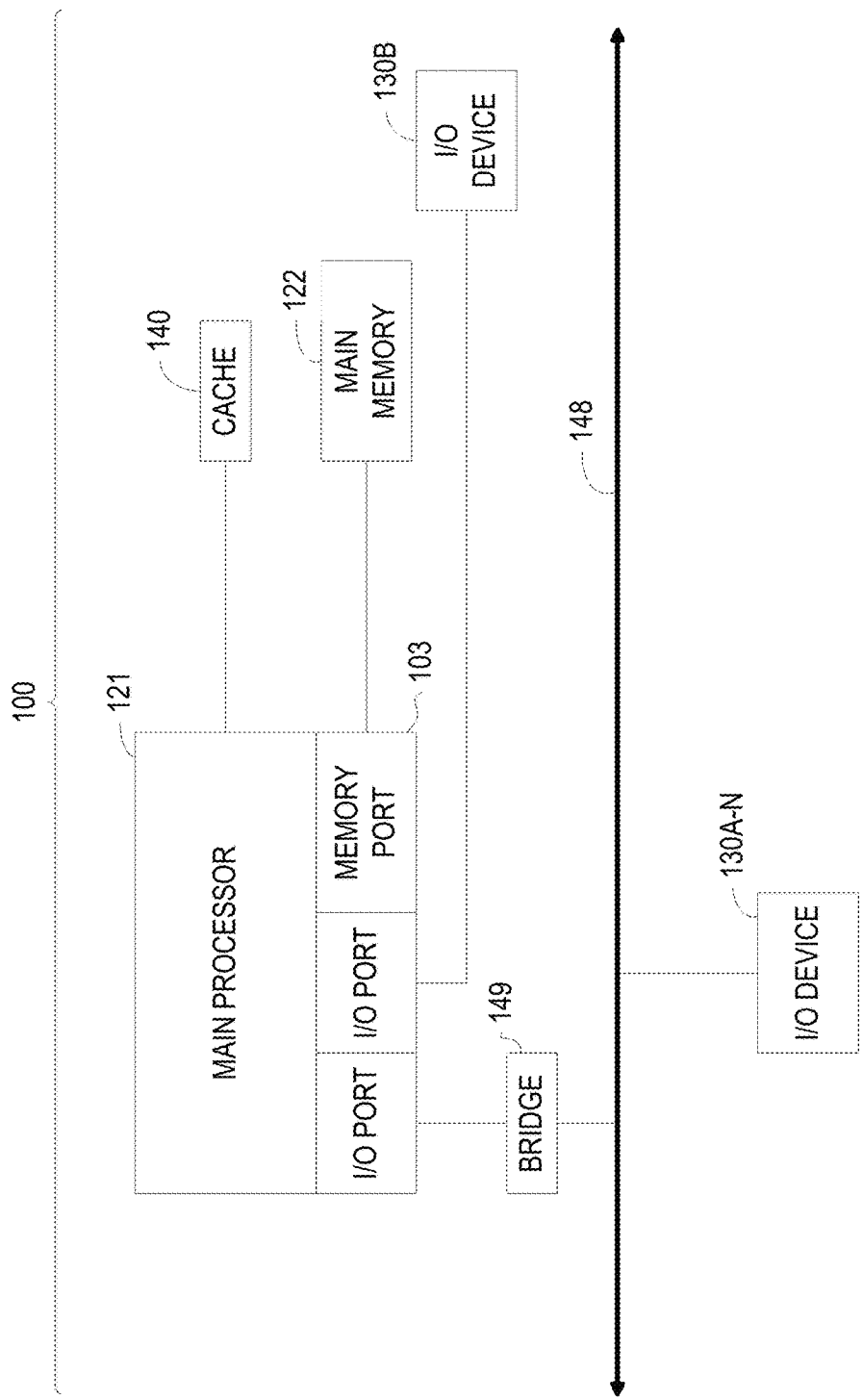

The client 102 and server 106 may be deployed as and/or executed on any type and form of computing device, e.g. a computer, network device or appliance capable of communicating on any type and form of network and performing the operations described herein. FIGS. 1G and 1D depict block diagrams of a computing device 100 useful for practicing an embodiment of the client 102 or a server 106. As shown in FIGS. 1G and 1D, each computing device 100 includes a central processing unit 121, and a main memory unit 122. As shown in FIG. 1G, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a wear detection module 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (REDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1G, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touch-screen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1G. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1G, the computing device 100 may comprise a storage device 128 (e.g. one or more hard disk drives or redundant arrays of independent disks) for storing an operating system or other related software, and for storing application software programs such as any program related to the software 120 for the experiment tracker system. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as a installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11E/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1F and 1G may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is a eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

C. Wearable Sensor Housing

Figure 2A:
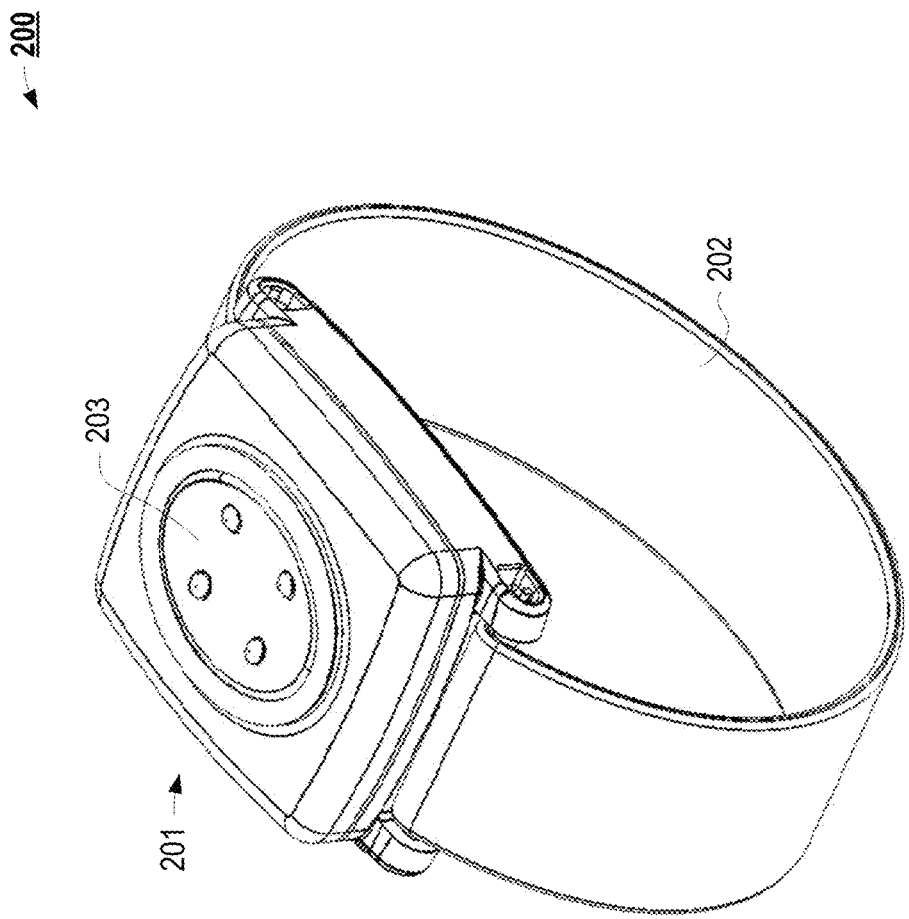
FIGS. 2A and 2B illustrate solid models of a wearable sensor.
Figure 2B:
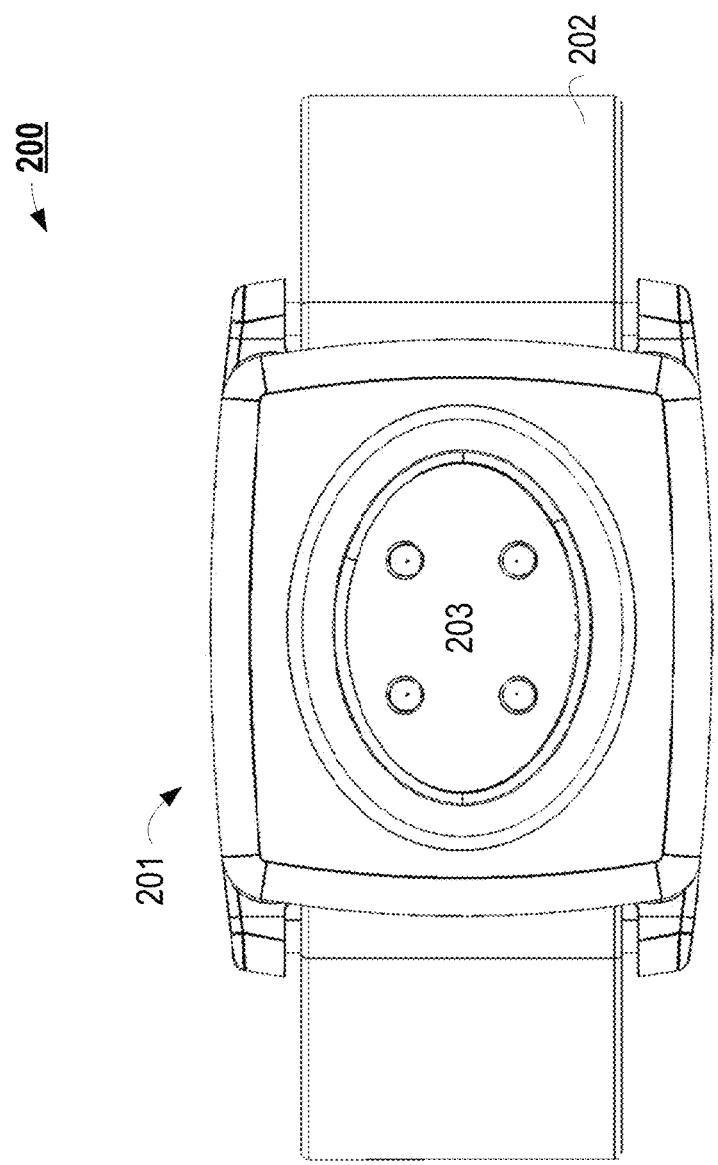

FIGS. 2A and 2B illustrate isometric and top views, respectively, of an exemplary wearable sensor 200. The wearable sensor 200 includes a housing 201, which is coupled to a user with a strap 202. In some implementations, a user may wear the wearable sensor 200 like a wrist watch. In other implementations, the wearable sensor 200 may include a clip, pin, or similar means to couple the wearable sensor 200 to a user. In some implementations, the wearable sensor 200 is incorporated into a watch or piece of jewelry (e.g., a bracelet or necklace).

The housing 201 houses the components described above in relation to FIG. 1A. The above described sensors 153 may be internal and/or external to the housing 201. For example, the wearable sensor 200 may include an accelerometer, which need not be exposed to the outside environment. In another example, the wearable sensor 200 may include an ambient light sensor that is exposed to the outside environment such that it can measure the light levels. Similarly, the wearable sensor 200 may include a galvanic response sensor on the bottom surface of the housing 201. The galvanic sensor may make contact with a user's skin and be configured to determine when it is in contact with a user's skin and when it is not in contact with a user's skin.

As illustrated, the wearable sensor 200 includes a button 203. In some implementations, the wearable sensor 200 includes a plurality of buttons and/or a screen. In some implementations, the screen is a touch screen. A user may use the bottom 203 to mark events. For example, a user may mark the beginning of physical activity. In some implementations, the button 203 is coupled to an input on the above described processor 121. When the button 203 is depressed, the processor 121 may mark the event. For example, the processor 121 may store a time stamp of when the button 123 was depressed in the storage device 128.

In some implementations, the wearable sensor 200 includes medical alert functionality. The button 203 may be used to request help or to send an alert that a medical incident is occurring. For example, if the user falls the user may press the button 203 and the wearable sensor 200 may send an alert to the client device 102 of a care taker.

In some implementations, the functionality of a button 203 and/or screen located on the wearable sensor 200 is achieved through a client device 102. For example, a user's smart phone may run an application that corresponds to the wearable sensor 200. The application may be in communication with the wearable sensor 200 through a data connection on the phone and wearable sensor 200. The application may provide the user with information relevant to the wearable sensor 200. In some implementations, the application may enable the user to activate features on the wearable sensor 200 as if the user was depressing a physical button on the wearable sensor 200. For example, the wearable sensor 200 may include an "activity button," that when activated causes the wearable sensor 200 to mark a time stamp indicating when the activity button was depressed in the application.

Figure 2C:
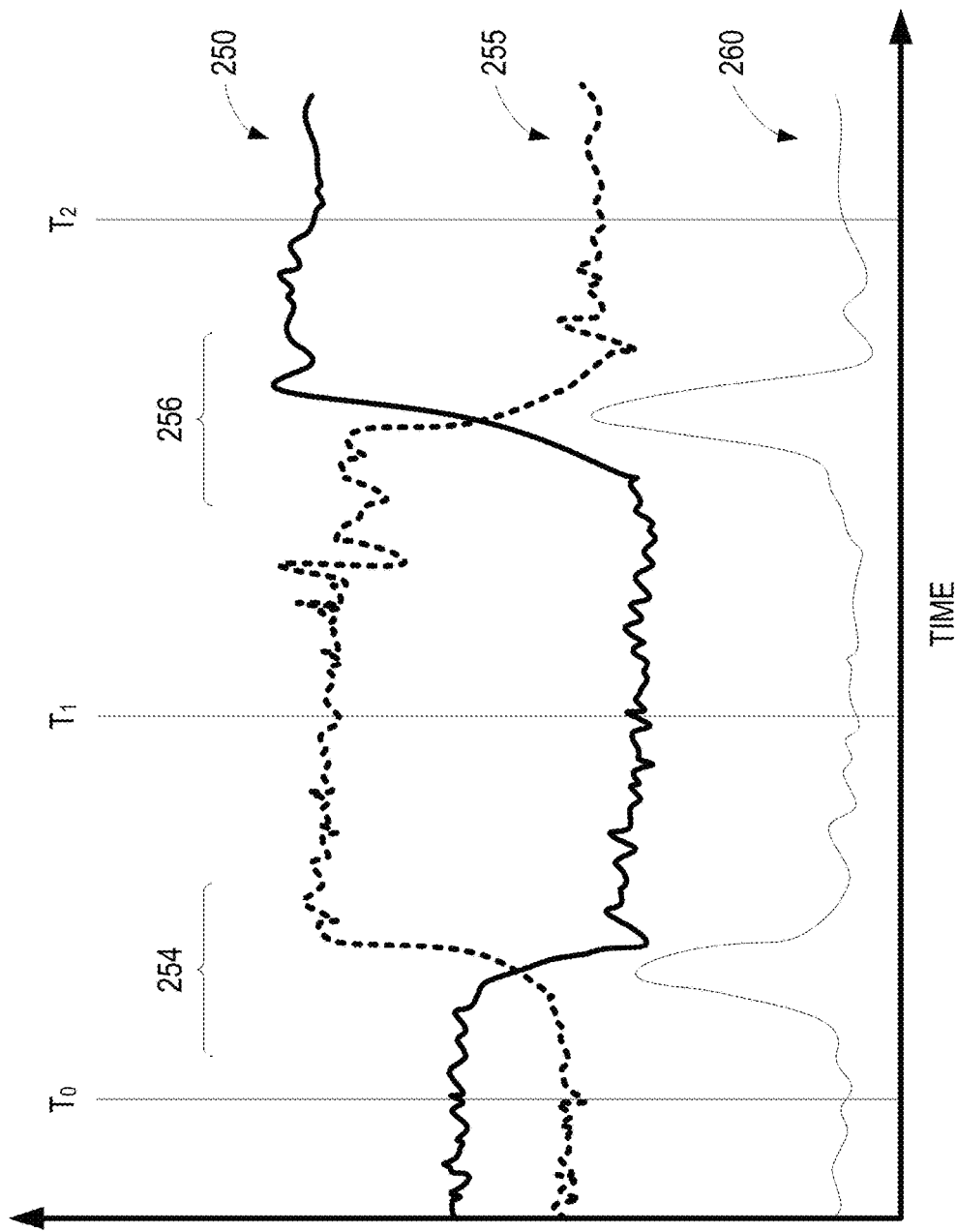
FIG. 2C is a graph illustrating data recorded with a wearable sensor.

The wearable sensor may be designed and constructed to have a predetermined shape or form that provides a predetermined orientation when the wearable sensor is lying at rest, falls and lies at rest or is placed down by the wearer on a surface. In some implementations, the wearable sensor 200 is configured such that when not worn, it defaults to a particular orientation. For example, the top of the housing 201 may be dome shaped and weighted to one side. When not worn the wearable sensor 200 may lean to the weighted side (also referred to as the wearable sensor's default orientation). When the wearable sensor 200 (or other device in the environment 180) detects the default orientation, the wearable sensor 200 may determine that it is not being worn. FIG. 2C depicts a graph of data that may be obtained with the wearable sensor 200. As described above, in some implementations, the wearable sensor 200 detects orientation. The solid line 250 indicates the wearable sensor's orientation along a first axis and the dotted line 252 indicates the wearable sensor's orientation along a second axis. The method of determining if movement has occurred based on orientation is described in greater detail below. In general, the change in orientation is correlated with a movement of the wearable sensor 200. For example, in the time epochs 254 and 256 relatively large fluctuations are seen in both the orientation signals 250 and 252. In some implementations, the wearable sensor 200 (or other device described herein) quantifies movement to determine if the wearable sensor 200 is being worn during different epochs.

In some implementations, basing the detection of movement on orientation enables sampling at a relatively lower sampling rate when compared to basing the detection of movement on acceleration. The line 260 indicates an acceleration signal of the same wearable sensor 200. As illustrated, the acceleration signal is relatively steady except for during epochs of large movement. However, to capture the rapid change in accelerations, the sampling frequency must be high enough to accurately recreate the signal. For example, if a sample is only recoded at $t_0$, $t_1$, and $t_2$, (far below the Nyquist frequency of the acceleration signal 260) then the acceleration signal would appear flat throughout the recording and it would appear as if no movement occurred. However, sampling at $t_0$, $t_1$, and $t_2$, provides data points with substantially different orientation values, and thus movement information may be determined from low sampled orientation data.

D. Context-Aware Transmission of Data from a Wearable Sensor

The systems and methods described herein are related to the context-aware transmission of data. In some implementations, by classifying data into predefined categories and then transmitting the data using a transmitter configuration associated with each of the categories enables improved transmission reliability while also improving battery life.

While the invention has been particularly shown and described with reference to specific embodiments, it should be understood by those skilled in the art that various changes in form and detail may be made therein without departing from the spirit and scope of the invention described in this disclosure. For example, the methods described herein may be included in as a module that is added to an already available wearable sensor or custom built wearable sensor such as the wearable sensor described herein.

Figure 3:
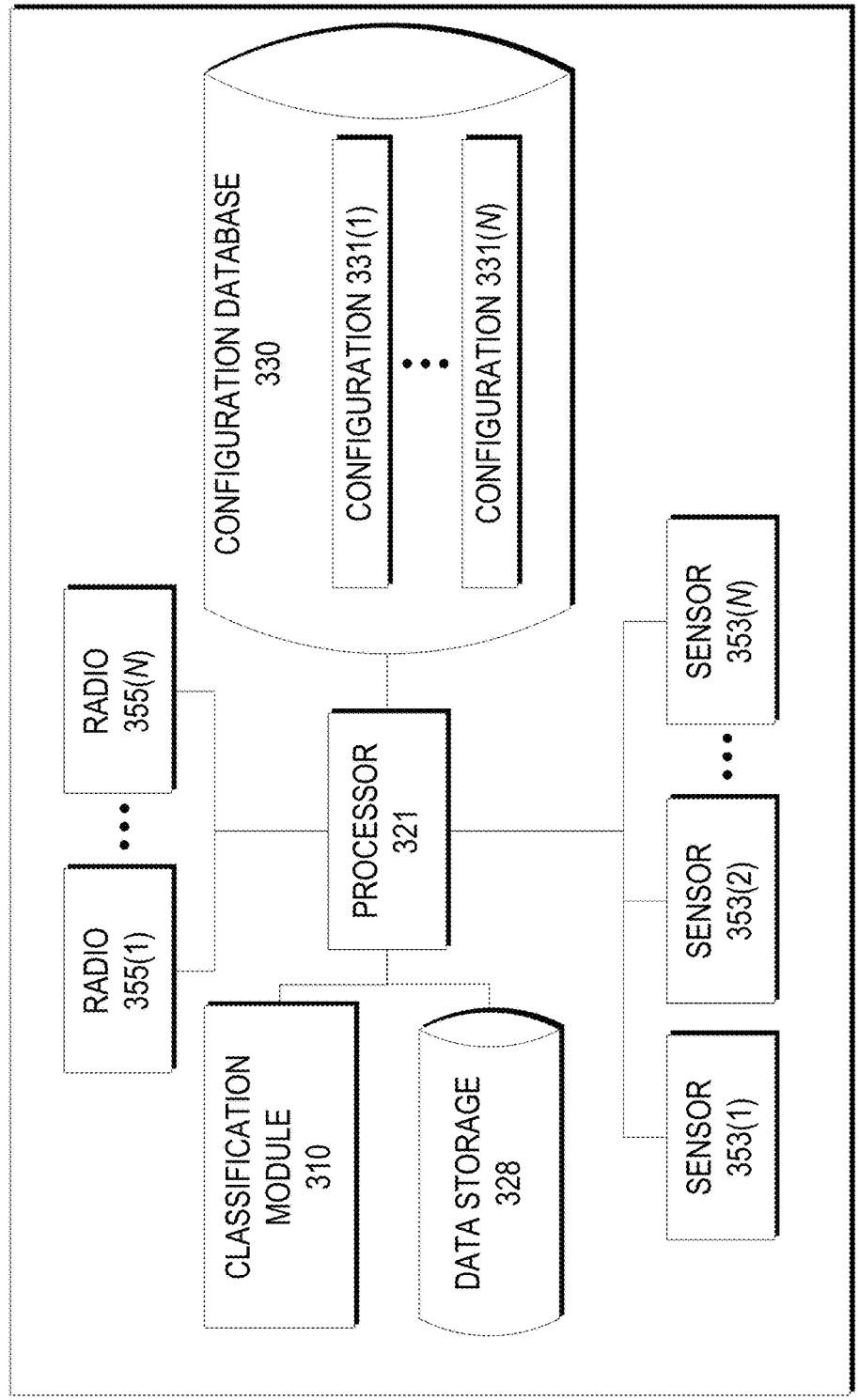
FIG. 3 is illustrates a block diagram of a schematic of an exemplary wearable sensor.

FIG. 3 depicts a schematic of an exemplary wearable sensor 300. The wearable sensor 300 is configured for the efficient transmission of data using context-aware transmission. The wearable sensor 300 includes one or more radios 355 (each of which include a transmitter and/or receiver), a storage device 328, a plurality of sensors 353(1)-353(N), and a processor 321. Each of these components are similar to the components described above in relation to FIGS. 1A-1G.

As set forth above, the wearable sensor 300 can include a plurality of sensors 353. In some implementations, the wearable sensor is a panic button and/or behavioral measurement device. The behavioral measurements may be based on the wearable sensor's orientation and/or movement. In some of these implementations, the orientation is determined my measuring the gravitational acceleration along the x, y, and z axis. The accelerometers can be configured to detect subtle movements, such as those that are difficult to spot with the naked eye. For example, the sensor 353 may detect movements that are caused by a user breathing or chewing. In some implementations, the sensors can detect orientation to within 1 degree, 0.5 degrees, or 0.01 degrees. In addition to movement, and as described above, the wearable sensor 300 may detect medical conditions of the wearer such as, but not limited to, temperature, pulse rate, and blood pressure. In some implementations, the sensors 353 can include altimeter sensors and/or frequency modulation (FM) tuners.

In some implementations, the processor 321 samples the signal generated by the sensors 353 at less than 10 Hz. For example, the processor 321 can sample the signal at about 1-5 Hz, about 3-7 Hz, or about 6-10 Hz. In some implementations, the processor 321 samples the signal as few as 1 sample per minute, 1 sample per 5 minutes, or 1 sample per 10 minutes. In yet other implementations, the processor 321 samples the signal above 10 Hz. For example, the processor 321 can sample the signal at about 10-50 Hz, about 50-100 Hz, about 100-200 Hz, about 200-1000 Hz.

To enable context-aware transmission of data, the wearable sensor 300 includes a classification module 310 and a configuration database 330. In some implementations, the classification module 310 is a stand-alone component of the wearable sensor 300 and, in other implementations, the classification module is a software module that is stored in the storage device 328 and executed by the processor 321. Similarly, the configuration database 330 may be stored in a storage device separate from storage device 328 or within storage device 328.

Now referring to the classification module 310 in greater detail, the classification module 310 classifies data into categories prior to transmission. The data is then transmitted responsive to the classification. Transmitting data responsive to a classification may include using a predetermined protocol stack (or transmission configuration) to transmit data of a particular category. The plurality of protocol stacks (i.e., radio or transmission configurations are discussed further in relationship to the configuration database 330). In general, the classification module 310, may divide data into a plurality of subsets and assign each subset of data to one of a plurality of categories.

In some implementations, as data is collected from the sensors 353 by the processor 321, the classification module 310 classifies the data in substantially real time. For example, the classification module 310 may classify the data as it is collected by the processor or the processor 321 may fill a buffer with collected data. When the buffer is substantially full, the classification module 310 may classify the data in the buffer into a category.

In other implementations, the classification module 310 classifies the data at a later point in time, such as just prior to transmission of the data. The classification module 310 can classify whole data sets or divide the data into individual subsets and classify each subset. The subsets may be created based on size, time steps, or a combination of both. For example, the classification module 310 may divide the data into subsets, each of which contain 64 kB of data. In another example, the classification module 310 may divided the data such that each subset of the data includes 10 minutes of data. In some implementations, the data may be classified responsive to the characteristics of the data (e.g., frequency or energy characteristics of the data, orientation of the wearable sensor, or intensity of the acceleration of the wearable sensor), the activity or state of the wearer when the data was recorded or a combination thereof. For example, the data may be classified as emergency data, routine data, high resolution data, fall data, sleep data, wake-up data, high-activity data, low activity data, moderate activity data, sedentary data, sitting data, walking data. The data may also be classified responsive to events such as out of range events, location change events, battery level indications, relative signal strength, or any combination thereof. The data may be classified based on high, medium, or low priority. As described further below, an example power configuration for emergency data may include a transmission configuration that consumes a relatively high level of power such that the wearable sensor can ensure the data is accurately received by a target device. In another example, a change of location event may be used to indicate to the wearable sensor that it is near a target device and may thus a low power transmission strength is acceptable to transmit the data to the nearby target.

Emergency data may include data associated with a medical emergency. For example, a fall may be classified as emergency data. In some implementations, the wearable sensor 300 may include a button, which the user can press in the event of an emergency. In some implementations, emergency data also includes high priority data. For example, a device malfunction may be classified as high priority data because it may be important that the wearable sensor 300 accurately notify a caretaker that a patient's wearable sensor 300 is no longer working properly. In some implementations, the transmission configurations associated with emergency data, high priority data, and/or control signals categories include parameters that enable reliable and relatively long range transmissions in comparison to the other categories. In some implementations, emergency data is automatically classified in substantially real time. For example, the wearable sensor can include an altimeter. If the altimeter determines there is a rapid change in altitude, the wearable sensor may determine the wearer of the wearable sensor fell and classify the data as emergency data. In some implementations, when data is classified as emergency data (or an emergency indicated by the user pressing a button on the wearable sensor) an indication of the emergency state, alternately to or in addition of the collected data, is sent to a second device. The second device can be any of the devices described in relation to FIG. 1C.

Routine data can include normal data recorded by the wearable sensor 300. Normal data may refer to the most common type of data present in a data set. For example, when the wearable sensor is used to collect activity data, a user is typically sedentary most of the day. Thus, sedentary (or low activity) data may be classified as normal (or routine) data.

High resolution data can include high activity data. For example, in some implementations, movement may be detected responsive to the wearable sensor's orientation. In a sedentary state, the wearable sensor 300 does not change orientation often. Accordingly, the wearable sensor's orientation may be recorded infrequently (or at a low resolution) and still provide an accurate portrait of the user's activity level. However, when active the wearable sensor's orientation may change frequently, and therefore the orientation signal would need to be sampled at a relatively high sampling frequency (or at a high resolution) to provide an accurate representation of the user's activity level. In some implementations, categories associated with high resolution data may include relatively higher frequencies and/or higher baud rates. As described below, the high frequencies and/or baud rates may enable relatively larger amounts of data to be transmitted without violating wireless transmission regulations.

In some implementations, the data is classified responsive to the area under the curve of the motion signal. The area under the curve may be calculated by differencing each data point with a running average of the motion signal. In other implementations, the data is classified responsive to the magnitude of a vector computed for each of the data points in the motion signal. In some implementations, the data is classified responsive to the differential (or slope) between data points in the wearable sensor's captured motion signal. For example, a histogram of the difference between consecutive motion samples may be used to classify the data. In this example, sedentary motion, or as termed above-normal data, does not include a high degree of variability between neighboring samples of the motion signal. Accordingly, a histogram of normal data's motion differential would substantially appear as a bell curve center near zero. A histogram of the high resolution data's motion differential, with its high degree of variability, may also appear as a bell curve; however, the histogram's center would be shifted away from zero.

The wearable sensor 300 also includes a configuration database 330, which stores a plurality of configurations 331. In some implementations, each category is associated with a different transmission configuration 331. A transmission configuration 331 can include a data encoding scheme, a bit packing scheme, a transmission protocol, or any combination thereof.

In some implementations, the data encoding scheme is an entropy encoding scheme. For example, the data can be included using Huffman encoding. Using entropy encoding, the size of an encoded data point is inversely proportional to its probability of occurring (i.e., the most common value is encoded with the fewest bits). As described above, the data can be classified responsive to the differential of the motion signal. In this embodiment, the value corresponding to the peak of the above described histograms is encoded with the fewest bits. In an simplified example, the most common value may be encoded as a 0, the second most common value as a 10, the third most common value as a 110, and the fourth most common value as a 111. The encoding scheme was applied to the differential signal; however, one of ordinary skill in the art will recognize that the scheme may also be applied to the raw motion signal, filtered data, summarized data, and/or other data that may be collected or derived by the wearable sensor 300.

When employing an entropy encoding scheme, the distribution of the data is used in encoding the data. In some implementations, the distribution is empirically calculated for each subset of the data being analyzed. For example, the processor 321 may determine and rank the occurrence of each value in the data subset. In other implementations, a distribution may be assigned to the data responsive to the selected category. An "average distribution" for each of the categories may be stored on the storage device 328 of the wearable sensor 300. The average distribution may be a predetermined distribution that is assigned to each category. The average distribution may approximate the distribution that is expected for a data set classified to a particular category. For example, it may be assigned that values $\{a_1, a_2, \ldots, a_n\}$ have a $\{P_1, P_2, \ldots, P_n\}$ probability of occurring. In embodiments employing predetermined average distributions, once classified into a particular data type, the predetermined average distribution is applied. For example, as described above, often the most common value of the differential of sedentary data (i.e., routine data) is zero. In this example, when the classification module 310 determines the data set is routine data, the processor 321 may automatically encode the value 0 as having the greatest probability of occurring, even if under empirical evaluation it is determined that the value 0 was not the most commonly occurring value. Employing that automatic application of the average distributions is computationally efficient relative to empirically determining the actual distribution of the data. In some implementations, the average distributions are revised or selected responsive to user's overall activity level, sex, age, medical condition, or any combination thereof.

The configurations 331(1)-331(N) also include parameters related to a transmission protocol. As described in detail below, generally the transmission configurations 331, in addition to an encoding scheme, include baud rate settings, transmission frequency settings, duty cycle settings, bandwidth settings, protocol settings, or any combination thereof. Below, each of these parameters are discussed in turn and then example configurations 331 as described.

In some implementations, each classification category is mapped to a predetermined transmission configuration 331. The configuration 331 may include settings and parameters that enable the data to be transmitted without violating national regulatory requirements. For example, in the United States the 315 MHz band is unlicensed, but regulated by the Federal Communications Commission (FCC). In general, transmissions within the 315 MHz band are restricted to control and safety applications. In these applications, the length of transmissions may not exceed two seconds per hour. The strength of the signal is also regulated to 75.6 dBµV/m measured at a distance of 3 meters. Non-control and safety signals (i.e., periodic data transmissions) in this band are allowed a maximum signal transmission length of one second, and the silence period must be at least thirty times the duration of the transmission, but not less than 10 seconds. The field strength of these transmissions is limed to 67.6 dBµV/m, as measured at a distance of 3 meters. Furthermore, the bandwidth of the signal when transmitting in the 315 MHz band cannot be wider than 787 kHz (0.25 percent of the operation frequency). Similar regulatory restrictions apply in countries outside the United States. Based on the methods and systems disclosed herein, one of ordinary skill in the art could set the transmission parameters such that they comply with local regulatory requirements.

In reference to the transmission frequency parameter that may be included in a configuration 331, the transmission frequency parameter may be any frequency used in the transmission of data. For example, the transmission frequency may be 70 MHz, 315 MHz, 433 MHz, 868 MHz, 900 MHz, 2.4 GHz, 5.8 GHz. In some implementations, a relatively lower transmission frequency is not as readily absorbed by environmental objects (e.g., walls) when compared to a high transmission frequency. The relatively lower transmission frequencies may also have a relatively larger range when compared to higher transmission frequencies. In some implementations, relatively lower frequencies require larger antennas when compared to higher frequencies. In some implementations, the transmission power may be -12 db, -6 db, 0 db, 6 db, or 12 db.

The configuration 331 may also include a baud rate and/or duty cycle of transmission (i.e., duration of the transmission) parameter. In some implementations, receiver sensitivity is inversely proportional to the transmission baud rate. For example, a relatively lower baud rate has a relatively higher receiver sensitivity. In some implementations, increasing the sensitivity of the receiver increases the effective range of the wearable sensor 300. As described above, the United States and other jurisdictions place restrictions on the duty cycle of a wireless transmission. Accordingly, when setting the baud rates for the configurations 331, the baud rate may be set as to not violate duty cycle requirements. For example, if 64 byte packets are transmitted with a baud rate of 0.5 Kbps the transmission time will extend past the regulatory requirements set by the FCC. However, if the baud rate is set to 38.4 Kbps, then the transmission time is within regulatory requirements. In some implementations, the lower baud rates also result in relatively greater battery usage, as the slow transmission rate means the wearable sensor is in an active transmission state for longer periods of time. In some implementations, the baud rate may be about 100-1000 bps, 1-50 Kbps, 50-500 Kbps, 500-1000 Kbps, 1000-10000 Kbps, 10-100 Mbps, or higher.

The configuration 331 may also include a wireless protocol. The wireless protocol may be a wide area network protocol (e.g., EDGE, LTE, HSPA, Wi-Fi, WiMax, UMTS, CDMA, or other cellular network protocol), local area network protocol (e.g., 802.11a/b/g/n/ac), or a personal area network protocol (e.g., Bluetooth, ZigBee, or MiWi).

In some implementations, the radios 355 are configurable to the parameters of each of the configurations 331. For example, responsive to receiving a configuration 331 that includes a frequency of 315 MHz and a baud rate of 0.5 Kbps, the base station can set its receiver to use the frequency 315 MHz and the baud rate 0.5 Kbps. In other implementations, the wearable sensor 300 may include a plurality of radios 355, each of which are preconfigured to correspond to one of the plurality of configurations 331(1)-331(N). For example, the wearable sensor may include three radios 355(1)-335(3) each of which correspond to a configuration 331(1)-331(3). In these implementations, when a configuration 331 is selected, the processor may not reconfigure a radio 355, but rather selected the appropriate radio 355 to use for data transmission. In some implementations, the base station can also include a plurality of pre-configured radios that correspond to each of the plurality of configurations 331(1)-331(N).

Using the above described parameters, a plurality of configuration 331 may be implemented. For example, a first configuration 331 may correspond to emergency data, a second configuration 331 may correspond to default or routine data, and a third configuration 331 may correspond to high resolution data. An example configuration 331 corresponding to emergency data may operate at a relatively low frequency range, with a low baud date, and a relatively high power setting. As described above, these parameters enable the emergency data to have relatively good penetration, high sensitivity, and good range. In some implementations, the wearable sensor's default configuration is substantially equivalent to the emergency configuration, such that in the case of an emergency the wearable sensor 300 does not first have to transmit a control signal to a receiver to change configurations 331.

In another example, losing data samples of high resolution data may not greatly affect the operation of the wearable sensor 300. An example configuration 331 for high resolution data may include a relatively high transmission frequency and baud rate and an average power level. In this example, the high transmission rate and baud rate enable the wearable sensor 300 to transmit the relatively larger amounts of data while remaining within regulatory requirements.

Figure 4:
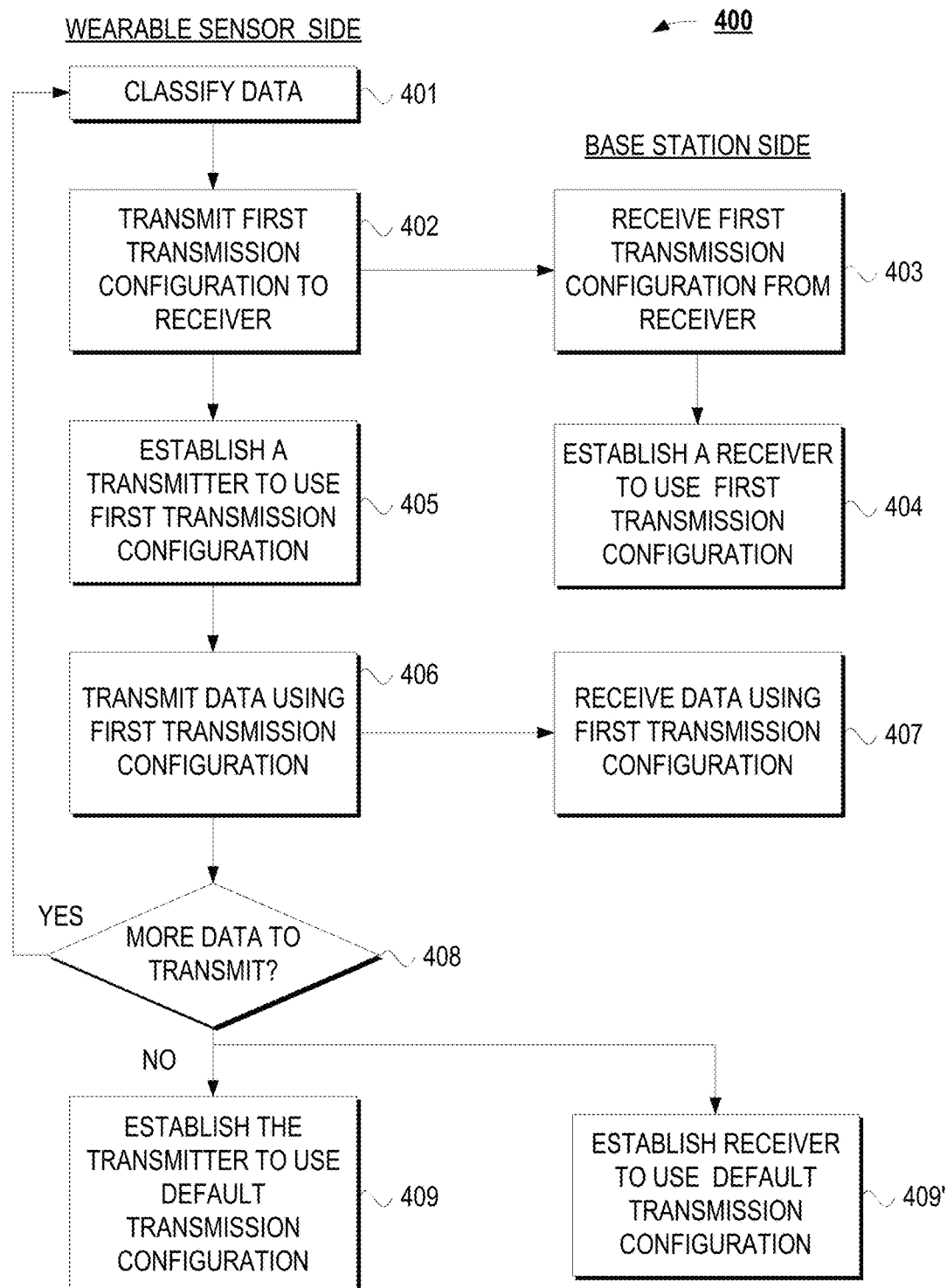
FIG. 4 is a flow chart of a method for transmitting data from a wearable sensor to a base station.

FIG. 4 depicts a flow chart of a method 400 for transmitting data from a wearable sensor to a base station or one of the other devices described in relation to FIG. 1C. The left hand side of the chart depicts steps that may be conducted by the wearable sensor, and the right hand side of the chart depicts steps that may be conducted by a base station (or other device).

The method 400 begins with the classification of the data (step 401). As described above, the data recorded by the wearable sensor is classified. In some implementations, the wearable sensor places recorded data into a buffer. Once the buffer is substantially filled, the wearable sensor classifies the data in the buffer. In other implementations, the wearable sensor storage recorded data into a storage device. At predetermined intervals, when instructed, or when a base station 160 is within range, the wearable sensor may retrieve data from its storage device for transmission. As described above, each classification is associated with a transmission configuration.

At step 402, an indication of the transmission configuration is sent to the base station. In some implementations, the indication of the transmission configuration is sent to the base station in using a default transmission configuration. Initially transmitting in a default configuration, may ensure that the base station is properly configured to receive the transmission from the wearable sensor. The indication of the transmission configuration may indicate to the base station which transmission configuration to use. For example, the base station may include a configuration database storing a plurality of configurations similar to the configuration database of the wearable sensor. In these implementations, the indication may indicate that the base station should set its radio to receive data using configuration X, where X is one of the N configurations stored in the base station's configuration database. In another implementation, the indication may include the parameters to which the base station should set its radio. For example, the indication may include the parameters: frequency: 315 MHz, power: −6 db, baud rate: 34.8 Kbps. In some of these implementations, the base station does not include a configuration database. At step 403, the indication is received by the base station. At step 404, the base station establishes its radio to use the configuration indicated by the transmitted indication.

At step 405, the wearable sensor establishes its radio to use the first configuration. As described above, establishing a radio to use a configuration may include setting the parameters of the radio to those indicated by the configuration and/or selecting a radio that is pre-configured to use the parameters of the configuration. In some implementations, the wearable sensor waits a predetermined amount of time between transmitting the indication of the first transmission configuration and beginning to transmit data using the first configuration. The predetermined amount of time may be selected to provide the base station with enough time such that it can properly configure its radio to receive data using the first transmission configuration.

At step 406 the data is transmitted to the base station by the wearable sensor, and at step 407 the data is received by the base station. In some implementations, the base station may store the received data in a storage device housed within the base station and/or transmit the data on to a second device. For example, the base station may receive the data and then forward the data on to a server for long term storage. In some implementations, the base station sends a confirmation back to the wearable sensor indicating that the data was properly received by the base station. The wearable sensor may attempt to retransmit the data to the base station if it does not receive the confirmation within a predetermined amount of time.

At step 408, the wearable sensor determines if there is more data to transmit to the base station. In some implementations, as described above, the wearable sensor transmits data as a memory buffer within the wearable sensor fills. In these implementations, the wearable sensor may wait until the buffer fills before restarting the method 400. In some implementations, the wearable sensor may retrieve data from a storage device and transmit subsets of the data to the base station. The subsets of data may be based on size (e.g., 64 Kb packets) or recording duration (e.g., 5 minutes of sensor data). The wearable sensor may classify each subset of data and iterate through the method 400 until all the subsets of data are transmitted to the base station. In some implementations, at step 408 the wearable sensor and the base station default back to the default transmission configuration, such that the indication of the transmission configuration for the next subset of data is sent from the wearable sensor to the base station using the default transmission configuration. In other implementations, the wearable sensor transmits the indication of the transmission configuration for the next subset of data to the base station using the previous transmission configuration.

At step 409 and 409', when the wearable sensor determines there is (temporally) no additional data to transmit to the base station, the wearable sensor establishes to use the default transmission configuration and the base station also establishes to also use the default configuration. In some implementations, establishing the default transmission configuration is responsive to a time out. For example, after a predetermined time out (i.e., a window when the wearable sensor does not transmit data and the base station does not receive data) the wearable sensor and base station default back to using the default transmission configuration. In some implementations, the wearable sensor informs the base station when it has concluded transmitting data to the base station, at which time the wearable sensor and base station can establish to use the default transmission configuration. In some implementations, the wearable sensor and base station may establish to use the default transmission configuration responsive to the base station sending a confirmation to the wearable sensor that it confirms receipt of substantially all the data transferred form the wearable sensor.

What is claimed:

1. A method for efficiently transmitting data from a wearable device, the method comprising:

classifying, by a wearable device with a transmitter configurable to transmit according to different transmission configurations, a first subset of data obtained by one or more sensors of the wearable device into a first category of a plurality of categories, each of the plurality of categories corresponding to one of a plurality of transmission configurations specifying at least a level of power at which the transmitter is to transmit;

establishing, by the wearable device, the transmitter to use a first transmission configuration corresponding to the first category, the first transmission configuration specifying a first level of power for transmitting the first subset of data;

encoding the first subset of data with a first encoding scheme based on the first category of the plurality of categories;

transmitting, by the transmitter, the first subset of data using the first level of power of the first transmission configuration;

establishing, by the wearable device responsive to classifying a second subset of data obtained by the one or more sensors of the wearable device into a second category of the plurality of categories, the transmitter to use a second transmission configuration of the plurality of transmission configurations corresponding to the second category, the second transmission configuration different from the first transmission configuration and specifying a second level of power, different than the first level of power, for transmitting the second subset of data;

encoding the second subset of data with a second encoding scheme different than the first encoding scheme based on the second category of the plurality of categories; and transmitting, by the transmitter, the second subset of data using the second level of power of the second transmission configuration.

2. The method of claim 1, further comprising transmitting, by the transmitter, to a receiver an indication of one of the first category or the first transmission configuration prior to transmitting the first subset of data.

3. The method of claim 1, further comprising transmitting, by the transmitter, to a receiver an indication of one of the second category or the second transmission configuration prior to transmitting the second subset of data.

4. The method of claim 1, wherein the first encoding scheme is specified by the first transmission configuration.

5. The method of claim 1, further comprising pausing a predetermined amount of time after transmitting to the receiver an indication of one of the first category or the first transmission configuration.

6. The method of claim 1, further comprising obtaining, by the wearable device, the data from measurements via a motion sensor within the wearable device.

7. The method of claim 1, wherein the first subset of data includes a plurality of data points, and the first subset of data is classified based on the differences between consecutive data points within the plurality of data points.

8. The method of claim 1, wherein each of the plurality of transmission configurations specify at least one of a baud rate, a transmission frequency, a duty cycle of transmission or a receiving filter bandwidth.

9. The method of claim 1, where classifying the first subset of data into the first category is responsive to a context associated with the first subset of data.

10. The method of claim 9, wherein the context is one of an age of a person wearing the wearable device, a time of day during which the first subset of data was captured, or an activity performed by the person wearing the sensor when the first subset of data was obtained.

11. The method of claim 1, wherein establishing the transmitter to use the first transmission configuration comprises selecting the transmitter from a plurality of different transmitters on the wearable device.

12. A wearable device comprising:
a transmitter configured to transmit according to different transmission configurations;
one or more sensors configured to detect a plurality of environmental parameters, physical activity parameters, behavioral parameters, or medical parameters; and
a processor configured to:
classify a first subset of data obtained by the one or more sensors wearable device into a first category of a plurality of categories, each of the plurality of categories corresponding to one of a plurality of transmission configurations specifying at least a level of power at which the transmitter is to transmit;
establish the transmitter to use a first transmission configuration corresponding to the first category, the first transmission configuration specifying a first level of power for transmitting the first subset of data;
encode the first subset of data with a first encoding scheme based on the first category of the plurality of categories;
transmit via the transmitter the first subset of data using the first level of power of the first transmission configuration;
establish, responsive to classifying a second subset of data obtained by the one or more sensors into a second category of the plurality of categories, the transmitter to use a second transmission configuration of the plurality of transmission configurations corresponding to the second category, the second transmission configuration different from the first transmission configuration and specifying a second level of power, different than the first level of power, for transmitting the second subset of data;
encoding the second subset of data with a second encoding scheme different than the first encoding scheme based on the second category of the plurality of categories; and
transmit, via the transmitter, the second subset of data using the second level of power of the second transmission configuration.

13. The wearable device of claim 12, wherein the processor is further configured to transmit, via the transmitter, to a receiver an indication of one of the first category or the first transmission configuration prior to transmitting the first subset of data.

14. The wearable device of claim 12, wherein the processor is further configured to transmit, via the transmitter, to a receiver an indication of one of the second category or the second transmission configuration prior to transmitting the second subset of data.

15. The wearable device of claim 12, wherein the first encoding scheme is specified by the first transmission configuration.

16. The wearable device of claim 12, wherein the processor is further configured to pause a predetermined amount of time after transmitting to the receiver an indication of the first category.

17. The wearable device of claim 12, wherein the processor is further configured to obtain the data via measurements from a motion sensor within the wearable device.

18. The wearable device of claim 12, wherein the processor is further configured to classify the first and second subsets of data based on the differences between consecutive data points within respective subsets of data.

19. The wearable device of claim 12, wherein each of the plurality of transmission configurations specify at least one of a baud rate, a transmission frequency, a duty cycle of transmission or a receiving filter bandwidth.

20. The wearable device of claim 12, wherein the processor is further configured to classify the first subset of data into the first category responsive to a context in which the first subset of data was recorded.

21. The wearable device of claim 20, wherein the context is one of an age of a person wearing the sensor, a time of day during which the first subset of data was captured, or an activity performed by the person wearing the sensor when the first subset of data was captured.

22. The wearable device of claim 12, wherein the processor is further configured to select a radio configured to use the first transmission configuration.

* * * * *